US008546487B2

(12) United States Patent
Kataoka et al.

(10) Patent No.: US 8,546,487 B2
(45) Date of Patent: Oct. 1, 2013

(54) CATIONIC POLY (AMINO ACIDS) AND USES THEREOF

(75) Inventors: Kazunori Kataoka, Tokyo (JP); Shourong Wu, Tokyo (JP); Takehiko Ishii, Tokyo (JP); HyunJin Kim, Tokyo (JP); Kanjiro Miyata, Tokyo (JP); Nobuhiro Nishiyama, Tokyo (JP)

(73) Assignee: The University of Tokyo, Tokyo (JP)

( * ) Notice: Subject to any disclaimer, the term of this patent is extended or adjusted under 35 U.S.C. 154(b) by 38 days.

(21) Appl. No.: 13/147,319

(22) PCT Filed: Feb. 15, 2010

(86) PCT No.: PCT/JP2010/052176
§ 371 (c)(1),
(2), (4) Date: Aug. 1, 2011

(87) PCT Pub. No.: WO2010/093036
PCT Pub. Date: Aug. 19, 2010

(65) Prior Publication Data
US 2012/0053295 A1    Mar. 1, 2012

(30) Foreign Application Priority Data

Feb. 13, 2009    (JP) .................................. 2009-031799

(51) Int. Cl.
*A61K 47/48* (2006.01)
*C08F 283/04* (2006.01)
*A01N 25/26* (2006.01)

(52) U.S. Cl.
USPC ........... 525/54.2; 525/420; 525/426; 424/418

(58) Field of Classification Search
None
See application file for complete search history.

(56) References Cited

U.S. PATENT DOCUMENTS

| | | | |
|---|---|---|---|
| 6,576,254 | B1 | 6/2003 | Uchegbu |
| 7,780,957 | B2 | 8/2010 | Kataoka et al. |
| 7,829,657 | B2 | 11/2010 | Kataoka et al. |
| 2004/0063618 | A1 | 4/2004 | Manoharan |
| 2007/0059271 | A1* | 3/2007 | Kataoka et al. .............. 424/78.3 |
| 2009/0258416 | A1 | 10/2009 | Kataoka et al. |
| 2009/0291130 | A1 | 11/2009 | Ohuchi et al. |
| 2010/0137512 | A1 | 6/2010 | Kataoka et al. |

FOREIGN PATENT DOCUMENTS

| | | |
|---|---|---|
| JP | 3 287545 | 12/1991 |
| JP | 2004 352972 | 12/2004 |
| WO | 99 61512 | 12/1999 |
| WO | 2004 099287 | 11/2004 |
| WO | 2005 078084 | 8/2005 |
| WO | 2006 085664 | 8/2006 |
| WO | 2007 099660 | 9/2007 |
| WO | 2008 010341 | 1/2008 |

OTHER PUBLICATIONS

International Search Report issued May 11, 2010 in PCT/JP10/052176 filed Feb. 15, 2010.
Miyata, K., et al., "Block Catiomer Polyplexes with Regulated Densities of Charge and Disulfide Cross-Linking Directed to Enhance Gene Expression," J. Am. Chem. Soc., vol. 126, pp. 2355-2361, (Feb. 6, 2004).
Miyata, K., et al., "Polyplexes from Poly(aspartamide) Bearing 1,2-Diaminoethane Side Chains Induce pH-Selective, Endosomal Membrane Destabilization with Amplified Transfection and Negligible Cytotoxicity," J. Am. Chem. Soc., vol. 130, pp. 16287-16294, (Nov. 12, 2008).
Extended European Search Report dated Sep. 21, 2012 from counterpart EP application No. 10 741 313.0, including Communication, European Search Opinion, European Search Report and examined claims 1-9.
Takae S et al, "PEG-Detachable Polyplex Micelles Based on Disulfide-Linked Block Catiomers as Bioresponsive Nonviral Gene Vectors", Journal of the Amercican Chemical Society (JACS), vol. 130, Sep. 4, 2008, pp. 6001-6009.
Szokan G & Kotai A, "Basische Derivate von Glutamylpeptiden, III", Acta Chimica Academiae Scientiarum Hungaricae, vol. 88. No. 2. 1976. pp. 137-147.
Makoto Oba et al, "Polyplex Micelles with Cyclic RGD Peptide Ligands and Disulfide Cross-Links Directing to the Enhanced Transfection via Controlled Intracellular Trafficking", Molecular Pharmaceutics, vol. 5, No. 6, Dec. 1, 2008, pp. 1080-1092.

\* cited by examiner

*Primary Examiner* — Robert M Kelly
(74) *Attorney, Agent, or Firm* — J-Tek Law PLLC; Jeffrey D. Tekanic

(57) ABSTRACT

The present invention provides an efficient delivery system for a nucleic acid, more specifically, a cationic poly(amino acid) that has a side chain having a plurality of different amine functional groups in a moiety including a cationic group and that has a hydrophobic group introduced into part of the side chain, and a polyion complex (PIC) of the poly(amino acid) and an oligo- or polynucleotide.

25 Claims, 9 Drawing Sheets

SEQUENCE LISTING

<160> NUMBER OF SEQ ID NOS: 4

<210> SEQ ID NO 1
<211> LENGTH: 21

```
<212> TYPE: RNA
<213> ORGANISM: Artificial Sequence
<220> FEATURE:
<223> OTHER INFORMATION: Description of Artificial Sequence: Synthetic
      sense strand of Homo sapiens siRNA for Bcl-2

<400> SEQUENCE: 1
caggaccucg ccgcugcaga c                                            21

<210> SEQ ID NO 2
<211> LENGTH: 23
<212> TYPE: RNA
<213> ORGANISM: Artificial Sequence
<220> FEATURE:
<223> OTHER INFORMATION: Description of Artificial Sequence: Synthetic
      antisense strand of Homo sapiens siRNA for Bcl-2

<400> SEQUENCE: 2
gucugcagcg gcgagguccu ggc                                          23

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      antisense strand of Homo sapiens siRNA for VEGF gene
<220> FEATURE:
<223> OTHER INFORMATION: Description of Combined DNA/RNA Molecule:
      Synthetic antisense strand of Homo sapiens siRNA for VEGF gene

<400> SEQUENCE: 3
ggaguacccu gaugagauct t                                            21

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      sense strand of Homo sapiens siRNA for VEGF gene
<220> FEATURE:
<223> OTHER INFORMATION: Description of Combined DNA/RNA Molecule:
      Synthetic sense strand of Homo sapiens siRNA for VEGF gene

<400> SEQUENCE: 4
gaucucauca ggguacucct t                                            21
```

US 8,546,487 B2

CATIONIC POLY (AMINO ACIDS) AND USES THEREOF

CROSS-REFERENCE

This application is the US national stage of International Patent Application No. PCT/JP2010/052176 filed on Feb. 15, 2010, which claims priority to Japanese Patent Application No. 2009-31799 filed on Feb. 13, 2009, the contents of which are hereby incorporated by reference into the present application.

TECHNICAL FIELD

The present invention relates to a cationic poly(amino acid) that has a hydrophobic group introduced into part of a side chain. More specifically, the present invention relates to a cationic poly(amino acid) that has a side chain having a plurality of different amine functional groups in a moiety including a cationic group and that has a hydrophobic group introduced into part of the side chain, and a polyion complex (PIC) of the poly(amino acid) and an oligo- or polynucleotide.

BACKGROUND ART

The application of siRNA to medical treatments is increasingly expected because the siRNA can knock down target mRNA specifically and effectively. However, the development of an effective delivery system is indispensable to apply the siRNA to medical treatments. In recent years, it has been clarified that a therapeutic effect of naked siRNA on age-related macular degeneration (CNV) through its intraocular administration under a clinical trial does not result from a sequence-specific gene knockdown effect induced by siRNA but results from a non-sequence-specific effect via recognition by Toll-like receptor-3 (TLR-3) on cell surface. It has been considered important to develop a carrier that is stable outside cells and is capable of accurately delivering siRNA into the cells in any of in vivo siRNA applications.

Poly(L-lysine) or polyethylene imine, which has been long known as a cationic polymer for forming a polyion complex (PIC) with DNA to introduce a gene into eukaryotic cells and expressing the gene, has a problem in that the compound does not exhibit very high gene expression efficiency or exhibits high toxicity on cells, for example. A wide variety of cationic polymers have been provided in order to solve such problem. For example, a poly(L-lysine) derivative in which a hydrophilic group (e.g., polyethylene glycol) and a hydrophobic group (e.g., palmitoyl) have been introduced via an ε-amino group of poly(L-lysine) forms a vesicle in the presence of cholesterol in an aqueous medium and the vesicle aggregates gene-containing plasmid DNA to form a stable complex (Patent Document 1). Further, a PIC formed of plasmid DNA with a copolymer derivative whose cation charge and disulfide crosslink density have been modulated by the thiolation of an ε-amino group of poly(L-lysine) in a poly(L-lysine)-poly(ethylene glycol) copolymer shows high stability in an extracellular medium and effectively releases the DNA in an intracellular compartment (Non Patent Document 1, some of the inventors of the present invention are coauthors of Non Patent Document 1). Further, the inventors of the present invention have confirmed, as part of such research, that, when poly(N—[N-(2-aminoethyl)-2-aminoethyl]aspartamide (PAsp (DET))) having an ethylenediamine structure in a side chain and a block copolymer including the PAsp (DET) as one block component of the block copolymer are produced, such polymers show low cytotoxicity and introduce plasmid DNA into cells with high efficiency to express a gene incorporated into the DNA efficiently (see Non Patent Document 2, Patent Document 2, and Patent Document 3).

PRIOR ART DOCUMENT

Patent Documents

[Patent Document 1] WO 99/61512
[Patent Document 2] WO 2006/085664 A1
[Patent Document 3] WO 2007/099660 A1

Non Patent Documents

[Non Patent Document 1] K. Mihata et al., J. Am. Chem. Soc. 2004, 126, 2355-2361
[Non Patent Document 2] K. Miyata et al., J. Am. Chem. Soc. 2008, 130, 16287-16294

SUMMARY OF INVENTION

Problem to be Solved by the Invention

PAsp(DET) and a block copolymer thereof disclosed in Patent Documents 2 and 3 exhibit low toxicity and high gene introduction efficiency on target cells to which a nucleic acid molecule is to be delivered, but as mentioned above, may not necessarily form a PIC having high stability under a physiological condition with a low molecular weight nucleic acid such as siRNA, which is increasingly expected for its application to medical treatments. Thus, an object of the present invention is to provide a synthetic polymer material which may serve as a carrier exhibiting higher stability with a low molecular weight nucleic acid such as siRNA under a physiological condition and exhibiting low toxicity and high gene introduction efficiency on target cells to which a nucleic acid molecule is to be delivered.

Means for Solving the Problem

This time, the inventors of the present invention have found that a cationic poly (amino acid) that has a side chain having a plurality of different amine functional groups in a moiety including a cationic group and that has a hydrophobic group introduced into part of the side chain exhibits no toxicity or little toxicity on target cells to which a nucleic acid molecule is to be delivered, and can form a stable PIC with a low molecular weight nucleic acid such as siRNA as well. The inventors have also found that the thus formed PIC forms a relatively monodispersed stable associate having an average diameter of a hundred-odd nm in an aqueous medium under a given condition, is incorporated into target cells with high efficiency, and exerts an effect inherently possessed by siRNA.

According to the present invention, the problem is solved by providing a poly(amino acid) derivative, which is represented by each of the following formula (1) and formula (2):

[Chem. 1]

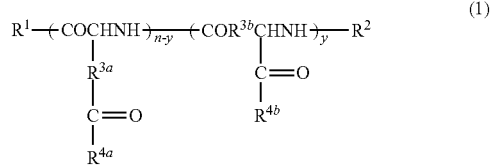

where: $R^1$ represents a hydroxyl group, an unsubstituted or substituted linear or branched alkyloxy group having 1 to 12 carbon atoms, an unsubstituted or substituted linear or branched alkenyloxy group having 2 to 12 carbon atoms, an unsubstituted or substituted linear or branched alkynyloxy group having 1 to 12 carbon atoms, or an unsubstituted or substituted linear or branched alkyl-substituted imino group having 1 to 12 carbon atoms;

$R^2$ represents a hydrogen atom, an unsubstituted or substituted linear or branched alkyl group having 1 to 12 carbon atoms, or an unsubstituted or substituted linear or branched alkylcarbonyl group having 1 to 24 carbon atoms;

$R^{3a}$ and $R^{3b}$ each independently represent a methylene group or an ethylene group;

$R^{4a}$ and $R^{4b}$ are each independently chosen from the same or different groups in the group consisting of the following groups:

$$-NH-(CH_2)_{p1}-[NH-(CH_2)_{q1}-]_{r1}NH_2 \quad (i);$$

$$-NH-(CH_2)_{p2}-N[-(CH_2)_{q2}-NH_2]_2 \quad (ii);$$

$$-NH-(CH_2)_{p3}-N\{[-(CH_2)_{q3}-NH_2] \\ [-(CH_2)_{q4}-NH]_{r2}H\} \quad (iii); \text{ and}$$

$$-NH-(CH_2)_{p4}-N\{-(CH_2)_{q5}-N[-(CH_2)_{q6}- \\ NH_2]_2\}_2 \quad (iv),$$

where: p1 to p4, q1 to q6, and r1 and r2 each independently represent an integer of 1 to 5;

5 to 40% of a total number of the group of each of $R^{4a}$ and $R^{4b}$ have at least one amino group in which a hydrogen atom is substituted by an acyl group having a saturated or unsaturated linear or branched aliphatic hydrocarbon residue having 6 to 27 carbon atoms, or a steroloxycarbonyl group;

n represents an integer of 30 to 5,000; and y represents an integer of 0 to 5,000, provided that, when $R^{3a}$ and $R^{3b}$ each represent a methylene group, y represents an integer smaller than n.

[Chem. 2]

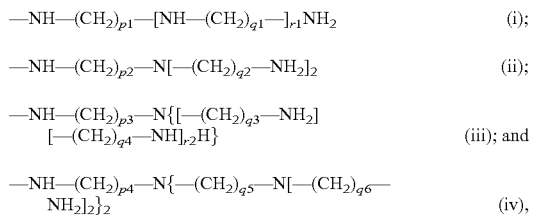

(2)

where: $R^2$, $R^{3a}$, $R^{3b}$, $R^{4a}$, $R^{4b}$, n, and y have the same meanings as those defined for the formula (1);

$L^1$ represents —S—S— or a valence bond;

$L^2$ represents —NH—, —O—, —O(CH$_2$)$_{p1}$—NH—, or -$L^{2a}$-(CH$_2$)$_{q1}$-$L^{2b}$-, where:

p1 and q1 each independently represent an integer of 1 to 5; $L^{2a}$ represents OCO, OCONH, NHCO, NHCOO, NHCONH, CONH, or COO; and $L^{2b}$ represents NH or O;

$R^5$ represents a hydrogen atom or an unsubstituted or substituted linear or branched alkyl group having 1 to 12 carbon atoms; and m represents an integer of 30 to 20,000.

Unless otherwise indicated, it should be understood that the groups or moieties in formula (1) and formula (2), or groups defined therefor are covalently bonded in the described directionality. In this regard, however, the arrangement of the repeating units having a number of repetitions n–y and the repeating units having a number of repetitions y in the above-mentioned formula (1) and formula (2) is arbitrary, and may be any structure such as a block structure, a random structure, or an alternating structure.

DESCRIPTION OF EMBODIMENTS

Figure 1:
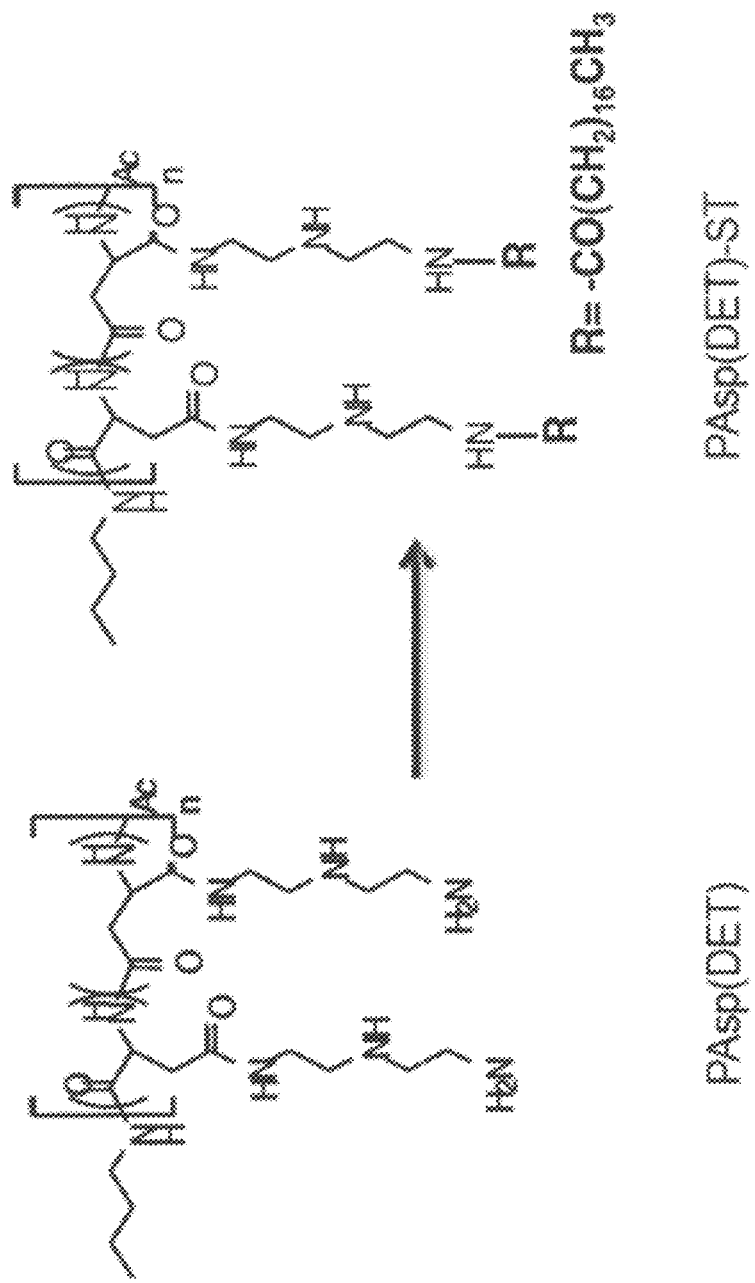
FIG. 1 is a diagram for illustrating the respective structural formulae of PAsp(DET) (on the left of the figure) and PAsp (DET)-ST manufactured by a method according to Example 1(1).

Hereinafter, the present invention is more specifically described.

Without wishing to be bound by theory, a cationic poly (amino acid) of the present invention has a side chain having a plurality of different amine functional groups in a moiety including a cationic group and thus exhibits pKa's at a plurality of stages. Under a physiological condition at pH 7.4, the plurality of amine functional groups are each in a partially protonated state and can form a polyion complex (PIC) through an interaction with a nucleic acid. Further, it can be understood that, when the PIC thus formed is taken up into the endosome (pH 5.5), the protonation of the cationic poly (amino acid) further proceeds owing to a decrease in pH and the promotion of endosome escape through a buffer effect (or proton sponge effect) alleviates damage on cells. Meanwhile, it is understood that, when a hydrophobic group is introduced into a moiety including a cationic group at a specific ratio, the introduction does not adversely affect the buffer effect (or proton sponge effect) and the PIC is stabilized through a hydrophobic interaction, and as a result, a relatively monodispersed stable associate having an average diameter of a hundred-odd nm is formed. Further, when the cationic poly (amino acid) as described above according to the present invention is used in the form of a block copolymer with a PEG segment in the same manner as described in Patent Document 3, the block copolymer can form a polymer micelle exhibiting satisfactory retentivity in circulating blood while at least retaining the characteristics possessed by the cationic poly (amino acid) itself.

The alkyl moiety in a linear or branched alkyl group, alkyl-substituted imino group, or the like having 1 to 12 carbon atoms, which is defined by the $R^1$ and $R^2$ in the formula (1) and formula (2), may be, for example, a methyl group, an ethyl group, an n-propyl group, an isopropyl group, an n-butyl group, an sec-butyl group, a tert-butyl group, an n-hexyl group, a decyl group, and an undecyl group. An alkenyl or alkynyl moiety in an unsubstituted or substituted linear or branched alkenyloxy group having 2 to 12 carbon atoms, an unsubstituted or substituted linear or branched alkynyloxy group having 1 to 12 carbon atoms, or the like may be exemplified by one including a double bond or a triple bond in the alkyl group having 2 or more carbon atoms as exemplified above.

For such group or moiety, a substituent in a "substituted" case may be exemplified by, but not limited to, a $C_{1-6}$ alkoxy group, an aryloxy group, an aryl $C_{1-3}$ oxy group, a cyano group, a carboxyl group, an amino group, a $C_{1-6}$ alkoxycarbonyl group, a $C_{2-7}$ acylamide group, a tri-$C_{1-6}$ alkyl siloxy group, a siloxy group, or a silylamino group, or may be exemplified by an acetalated formyl group, a formyl group, or a halogen such as chlorine or fluorine. In this context, for example, the expression "$C_{1-6}$" means 1 to 6 carbon atoms and is used with the same meaning in the following description. In addition, an unsubstituted or substituted linear or branched alkyl moiety having 1 to 12 carbon atoms in the unsubstituted or substituted linear or branched alkylcarbonyl group having 1 to 24 carbon atoms may be selected with reference to the examples, and an alkyl moiety having 13 or more carbon atoms may be, for example, a tridecyl group, a tetradecyl group, a pentadecyl group, a nonadecyl group, a docosanyl group, and a tetracosyl group.

As for the methylene group or the ethylene group in the definition for $R^{3a}$ and $R^{3b}$, it is understood that, when both of $R^{3a}$ and $R^{3b}$ each represent a methylene group, a repetitive unit involving such definition represents a unit derived from poly(aspartic acid), and the respective units having those groups are present at random. Meanwhile, when both of $R^{3a}$ and $R^{3b}$ each represent an ethylene group, a repetitive unit involving such definition represents a unit derived from poly (glutamic acid), and in this case, represents a polymer in which y represents an integer of 0 or n-y represents an integer of 0. The former represents, for example, a unit derived from poly-α-glutamic acid obtained by the polymerization of glutamic acid γ-benzyl ester N-carboxylic anhydride. Meanwhile, the latter represents, for example, a unit derived from poly-γ-glutamic acid produced by a bacterial strain belonging to the genus *Bacillus* bacteria such as *Bacillus natto*.

The group chosen from the group consisting of:

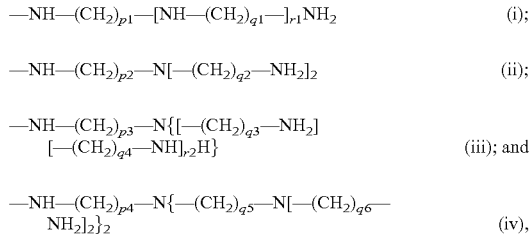

which is defined for the group of each of $R^{4a}$ and $R^{4b}$, is preferably the same group, and p1 to p4 and q1 to q6 each independently represent preferably 2 or 3, more preferably 2. Meanwhile, r1 and r2 each independently represent preferably an integer of 1 to 3.

In the group of each of $R^{4a}$ and $R^{4b}$, a hydrogen atom of at least one amino group in the group accounting for 5 to 40%, preferably 10 to 30%, more preferably 15 to 25% of the total number n-y or y of the group is substituted by an acyl group having a saturated or unsaturated linear or branched aliphatic hydrocarbon residue having 6 to 27 carbon atoms, or a steroloxycarbonyl group. When the aliphatic hydrocarbon residue is saturated, the residue is equivalent to an alkyl group having 6 to 27 carbon atoms and is exemplified by a pentacosyl group, a hexacosyl group, or a heptacosyl group as well as the alkyl group. The unsaturated aliphatic hydrocarbon residue corresponds to a group in which 1 to 5 carbon-carbon single bonds in a chain of the alkyl group are replaced by carbon-carbon double bonds. An acyl group (RCO—) having such residue (R) may be exemplified by, but not limited to, lauric acid (or dodecanoic acid), myristic acid (or tetradecanoic acid), palmitic acid (or hexadecanoic acid), palmitoleic acid (or 9-hexadecenoic acid), stearic acid (or octadecanoic acid), oleic acid, linoleic acid, linolenic acid, eleostearic acid (or 9,11,13-octadecatrienoic acid), arachidic acid, arachidonic acid, behenic acid, lignoceric acid, nervonic acid, cerotic acid, or montanic acid.

The sterol used herein means a natural, semisynthetic, or synthetic compound based on a cyclopentanone hydrophenanthrene ring ($C_{17}H_{28}$) and derivatives thereof. For example, a natural sterol is exemplified by, but not limited to, cholesterol, cholestanol, dihydrocholesterol, cholic acid, campesterol, or sitosterol. Semisynthetic or synthetic compounds thereof may be, for example, synthetic precursors of these natural products (as necessary, encompassing a compound in which part or all of, if present, certain functional groups, hydroxy groups have been protected with a conventional hydroxy protective group, or a compound in which a carboxyl group has been protected with carboxyl protection). Further, the sterol derivative means that, for example, without adversely affecting the object of the present invention, a $C_{1-12}$ alkyl group, a halogen atom such as chlorine, bromine, or fluorine may be introduced into a cyclopentanone hydrophenanthrene ring, and the ring system may be saturated or partially unsaturated. A redidue of the sterol derivative is preferably a group in which a hydrogen atom of a hydroxy group at the 3-position of cholesterol, cholestanol, or dihydroxycholesterol has been removed. The residue is more preferably a group in which a hydrogen atom of a hydroxy group at the 3-position of cholesterol has been removed. A sterol of the steroloxycarbonyl group is exemplified by one of an animal or vegetable oil origin such as cholesterol, cholestanol, dihydro cholesterol, cholic acid, campesterol, or sitosterol.

n, which represents the number of repetitive units of an amino acid, may represent 30 to 5,000, and in view of convenience in synthesis, may represent 30 to 300, preferably 60 to 150, more preferably 60 to 100. Further, y may represent 0 to 5,000, and in view of convenience in synthesis, may represent 30 to 300, preferably 60 to 150, more preferably 60 to 100.

According to the present invention, there can also be provided a block copolymer represented by the formula (2). In the formula (2), $R^2$, $R^{3a}$, $R^{3b}$, $R^{4a}$, $R^{4b}$, n, and y in the formula same meanings as those defined for the formula (1) and described above.

$L^1$ represents —S—S— or a valence bond. Meanwhile, $L^2$ represents —NH—, —O—, —O(CH$_2$)$_{p1}$—NH—, or -$L^{2a}$-(CH$_2$)$_{q1}$-$L^{2b}$-, where: p1 and q1 each independently represent an integer of 1 to 5; $L^{2a}$ represents OCO, OCONH, NHCO, NHCOO, NHCONH, CONH, or COO; and $L^{2b}$ represents NH or O. $L^1$ and $L^2$ need to be combined with each other so that they may form one linking group. For example, when $L^2$ represents —NH—, $L^1$ does not represent —S—S— but a valence bond. Preferred -$L^1$-$L^2$- is one forming a linking group in the case where $L^1$ represents —S—S—.

$R^5$ represents a hydrogen atom or an unsubstituted or substituted linear or branched alkyl group having 1 to 12 carbon atoms. As examples thereof, ones described for $R^1$ are applied. m, which represents the number of repetitive units of ethylene glycol (or oxyethylene), represents an integer of 30 to 20,000, preferably 200 to 2,000, more preferably 500 to 1,000.

The poly(amino acid) represented by the formula (1) may be manufactured, for example, by: subjecting a polyamino acid ester, which is manufactured by the polymerization of a conventional N-carboxylic anhydride derived from an aspartic acid ester or a glutamic acid ester, to aminolysis using a polyamine corresponding to a polyamine residue of the group of each of $R^{4a}$ and $R^{4b}$ to introduce the polyamine residue into a side chain of the poly(amino acid); and subjecting an amino group of a polyamine moiety thus introduced to a reaction with an appropriate amount of an activated carboxylic acid, which is obtained by the activation of a carboxyl group of a carboxylic acid corresponding to an acyl group having the aliphatic hydrocarbon residue, if required. The block copolymer of the formula (2) may be manufactured in accordance with a conventional linking method for a polyethylene glycol segment and the poly(amino acid) manufactured as described above, or may be manufactured in accordance with the method described in Non Patent Document 3 including manufacturing a block copolymer that has the polyamine residue being free from a hydrophobic group and then carrying out a reaction with an activated carboxylic acid. The introduction of a hydrophobic group excluding the acyl group may also be carried out by a conventional reaction of an amino group and an active carbonate esterified product carrying the hydrophobic group.

The polymers of the formula (1) and the formula (2) which may be provided as described above exhibit the pKa's at a plurality of stages, and hence can form a polyion complex (PIC) with an anionically chargeable compound under a physiological condition. The anionically chargeable compound may be a protein, a lipid, a peptide, or a nucleic acid. In particular, a PIC with a nucleic acid is conveniently formed. Hence, hereinafter, a PIC of a nucleic acid and a cationic poly(amino acid) of the present invention or a block copolymer thereof is described for the purpose of simplifying the description.

As described above, the cationic poly(amino acid) of the present invention has a hydrophobic group in its side chain, and hence the cationic poly(amino acid) can form a PIC with a small molecular weight nucleic acid as well under a physiological condition to provide a stable vesicle or associate. The nucleic acid capable of providing a PIC in accordance with the present invention using the cationic poly(amino acid) of the formula (1) or block copolymer of the formula (2) means a poly- or oligonucleotide including as a basic unit nucleotides formed of a purine or pyrimidine base, a pentose, and phosphoric acid, and examples thereof may include oligo- or poly-double-stranded RNA, oligo- or poly-double-stranded DNA, oligo- or poly-single-stranded DNA, and oligo- or poly-single-stranded RNA. Further, oligo- or poly-double-stranded nucleic acid and oligo- or poly-single-stranded nucleic acid in each of which RNA and DNA exist in a mixed state in the same chain are also included. Further, the nucleotide contained in the nucleic acid may be of natural type or of chemically modified non-natural type, or may have added thereto an amino group, a thiol group, a fluorescent compound, or any other molecule. The nucleic acid is not limited but may be formed of 4 to 20,000 bases, preferably 10 to 10,000 bases, more preferably 18 to 30 bases. Further, in consideration of functions or actions, there may be given plasmid DNA, siRNA, micro RNA, shRNA, an antisense nucleic acid, a decoy nucleic acid, an aptamer, and a ribozyme.

As the siRNA, for example, all of those designed for a gene or a polynucleotide of interest by a conventional method may be used. For the chain length of siRNA, a moiety for forming a double strand may have a length of preferably 15 to 50 bases, more preferably 18 to 30 bases, and conventional compounds and all nucleotides having the same actions or functions as those compounds are encompassed. Specific examples of the siRNA may be designed with reference to a gene which may serve as a target of a gene therapy, but are not limited thereto. Examples of such gene may include, but not limited to, PKCα related to a disease such as non-small cell lung carcinoma, BCL-2 related to a disease such as malignant melanoma, ICAM-1 related to Crohn's disease, HCV related to C type hepatitis, TNFα related to rheumatoid arthritis or psoriasis, adenosine AI receptor related to asthma, c-raf kinase related to a disease such as ovary cancer, H-ras related to a disease such as pancreas cancer, c-myc related to coronary artery disease, PKA Riα related to large bowel cancer, HIV related to AIDS, DNA methyl transferase related to solid cancer, VEGF receptor related to cancer, ribonucleotide reduction enzyme related to kidney cancer, CMV IE 2 related to CMV retinitis, MMP-9 related to prostate cancer, TGFβ2 related to malignant glioma, CD 49 d related to Multiple Sclerosis, PTP-1B related to diabetes, c-myb related to cancer, EGFR related to a disease such as breast cancer, and mdr1, autotaxin and GLUT-1 gene related to cancer. As for the antisense nucleic acid, those known in the art or all having the same functions or actions as those may be employed as a target for forming a PIC in accordance with the present invention.

Thus, the PIC of the nucleic acid and the compound represented by the formula (1) or the formula (2) as described above is provided as another aspect of the present invention. Such PIC of the compound of the formula (1) or the formula (2) and for example, siRNA may be stable under a physiological condition generally when the N/P ratio is 2 to 60.

The definition N/P ratio=[total number of amino group and substituted amino group of polycation moiety in side chain]/[total number of phosphate group in nucleic acid] is applicable.

As for the compound of the formula (1), an optimum N/P ratio varies depending on the ratio of the hydrophobic group in the total amino group and hence cannot be specified. In general, however, when a PIC with siRNA is formed so that the N/P ratio is 5 or more, preferably 7 or more, a stable associate having an average particle diameter size of about one hundred and several tens nm can be provided under a physiological condition such as in circulating blood. Such PIC can be prepared by mixing the compound of the formula (1) and siRNA in an aqueous solution buffered as necessary so as to achieve the N/P ratio. When the block copolymer of the formula (2) is used, and in particular, the ratio of a hydrophobic group is increased, there is a tendency that such copolymer alone associates autonomously in an aqueous solution to form a polymeric micelle. Thus, a stable PIC can be formed at a wider range of N/P ratios as compared to the case of using the compound of the formula (1).

Hereinafter, the present invention is further described by way of specific examples. However, these examples are provided for illustrative purposes only.

Production Example 1

Synthesis of N-succinimidyl octadecanoate

N-Succinimidyl octadecanoate was synthesized in accordance with the following article [N. M. Howarth, W. E. Lindsell, E. Murray, P. N. Preson, Tetrahedron 61 (2005) 8875-8887.]. Stearic acid (1.87 g, 6.56 mmol) and N-hydroxysuccinimide (0.76 g, 6.56 mmol) were dissolved in 80 mL of dichloromethane (DCM) and subjected to a reaction with 1-ethyl-3-(3-dimethylaminopropyl)-carbodiimide hydrochloride (WSC) (1.25 g, 6.56 mmol) for 48 hours. The reaction product was then washed with water, extracted with DCM twice, and dried over $MgSO_2$ to afford a white powder (1.4 g, 56% yield). The conversion rate of a carboxyl group in stearic acid was calculated by $^1$H-NMR and found to be 96%.

Example 1

(1) Synthesis of Stearoyl Group-Introduced PAsp(DET) (PAsp(DET)-ST)

β-Benzyl-L-aspartate-N-carboxylic anhydride (BLA-NCA) was subjected to cleavage polymerization using n-butylamine as an initiator to synthesize poly(β-benzyl-L-aspartate) (PBLA) (polymerization degree: 110). Next, PBLA (513 mg) was lyophilized from benzene and then dissolved in 25 mL of N-methyl-2-pyrrolidone (NMP). A 50-fold equivalent of diethylenetriamine (DET) with respect to a PBLA side chain was mixed with 13.5 mL of NMP. Then, under argon at 10° C., the DET solution was added to the PBLA solution and the mixture was subjected to a reaction for 1 hour. After that, the resultant was added to a cooled 0.01 N HCl aqueous solution, dialyzed against 0.01 N HCl twice, dialyzed against water at 4° C., and then collected by lyophilization. Confirmation has been made that PAsp(DET) (on the left of FIG. 1) thus synthesized has a high buffer ability while having a cell membrane damaging activity in response to a low pH environment, and can transport plasmid DNA into the cytoplasm efficiently (see Non Patent Document 2). Next, PAsp(DET) (100 mg, 0.366 mmol in terms of the molar number of an Asp(DET) unit) and DIPEA (638 ml, 3.66 mmol) were dissolved in 6 mL of methanol and subjected to a reaction with N-succinimidyl octadecanoate (27.8 mg, 0.073 mmol) dissolved in 6 mL of DCM at 4° C. for 24 hours. After the reaction, the reaction product was reprecipitated in diethyl ether and filtered. The resultant sample was dissolved in methanol/water (1:1 v/v) and then dialyzed at 4° C. against a 0.01 M HCl aqueous solution three times and distilled water once. After that, the resultant was collected by lyophilization to synthesize PAsp(DET)-ST having a stearoyl group introduced into a side chain (on the right of FIG. 1). The yield of the polymer was 90% or more.

(2) Complex Formation of PAsp(DET)-ST and siRNA

Figure 2:
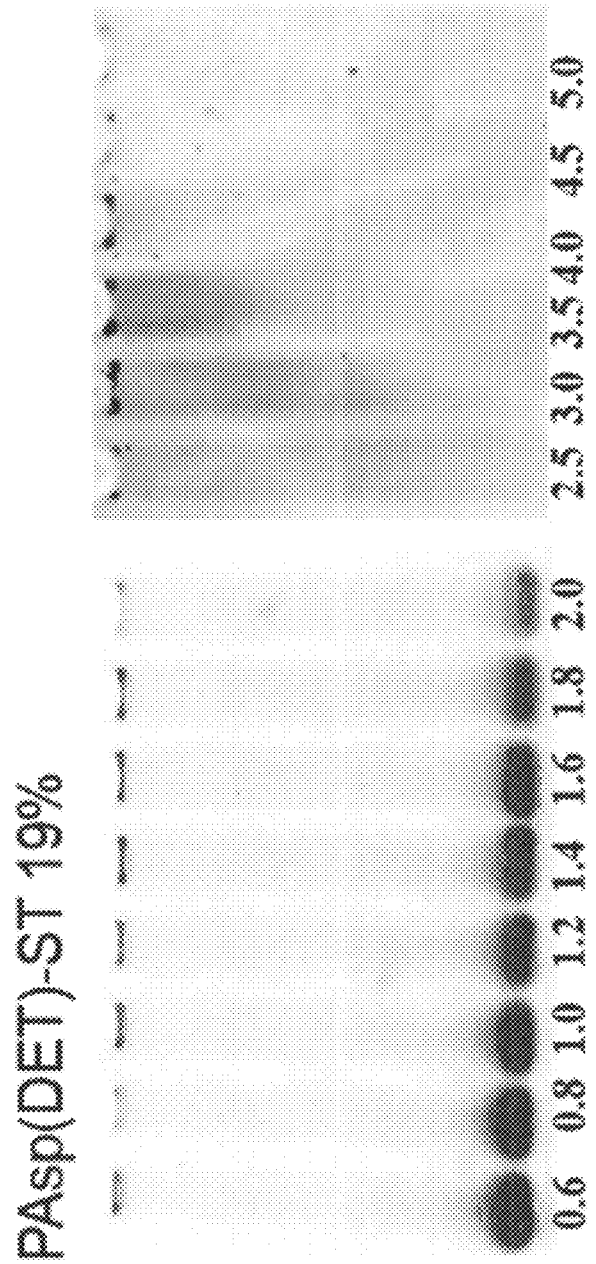
FIG. 2 is a photograph as an alternative of a diagram for showing the results of polyacrylamide gel electrophoresis of a PIC of PAsp(DET)-ST 19% and siRNA formed by a method according to Example 1(2).
Figure 3:
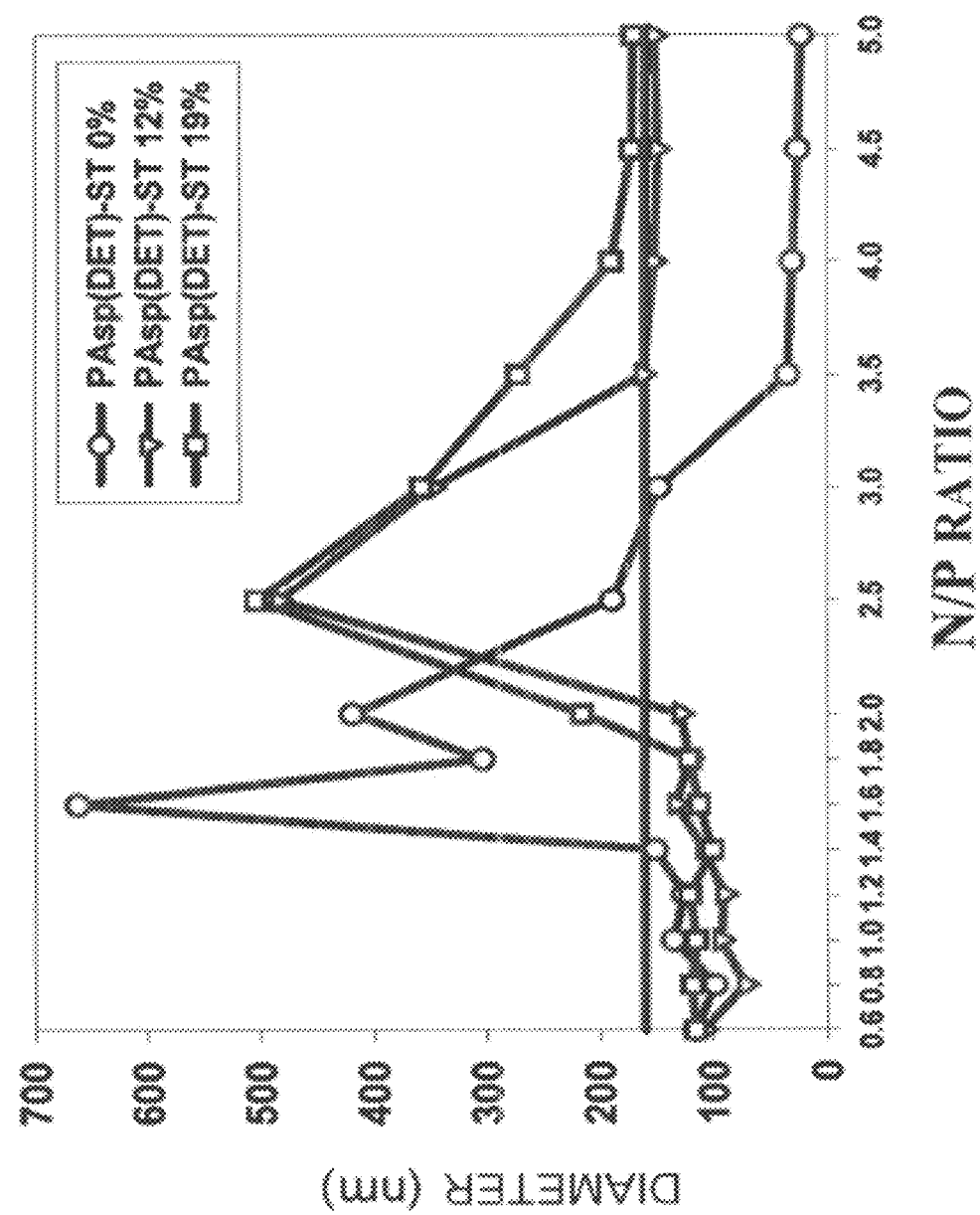
FIG. 3 is a graph illustrating the evaluation results of the particle diameter and polydispersity index of the PIC of Example 1(2) by dynamic light scattering. At N/P=5.0, an ST 12% micelle had an average size of 171 nm and a polydispersity index (PDI) of 0.144, whereas an ST 19% micelle had an average size of 152 nm and a polydispersity index of 0.100.

PAsp(DET)-ST having a stearoyl group introduction rate of 0, 12, or 19% was dissolved in a 10 mM HEPES buffer (pH 7.3) or a 50% ethanol solution (ethanol/10 mM Hepes buffer, 1:1 v/v) and mixed with siRNA (20 μM, 10 mM HEPES buffer (pH 7.3)) at different N/P ratios. Complex formation was confirmed by polyacrylamide electrophoresis (FIG. 2 illustrates the results of electrophoresis of complexes of PAsp (DET)-ST 19% and siRNA). As a result, in the case of using any polymer, a band of free siRNA disappeared at an N/P ratio equal to or more than a specific value (N/P ratio of 2.5 or more in the case of PAsp(DET)-ST 19%), suggesting that the complex formation of siRNA with PAsp(DET) or PAsp(DET)-ST occurred. Next, PAsp(DET)-ST/siRNA was evaluated for its particle diameter and polydispersity index (PDI) by dynamic light scattering (Dynamic light scattering Zetasizer (Malvern Instruments, Worcestershire, U.K.)) (FIG. 3). As a result, a large aggregate having a size of 200 nm or more was formed at a relatively low N/P ratio (N/P ratio of 1.4 to 2.5 in the case of PAsp(DET) and N/P ratio of 2.0 to 3.5 in the case of PAsp(DET)-ST), whereas a relatively monodispersed associate having a size of 150 to 170 nm was formed only in the case of PAsp(DET)-ST at an N/P ratio of 3.5 to 4.0 or more. On the other hand, in the case of PAsp(DET), scattered light intensity was weak and no associate formation was confirmed.

The above-mentioned results suggest that the introduction of a stearoyl group as a hydrophobic group into a PAsp(DET) side chain led to complex stabilization through a hydrophobic interaction and nanoparticle formation.

Example 2

(1) Knockdown of Endogenous Gene Bcl-2 with PAsp(DET)-ST/siRNA Complex

Figure 4:
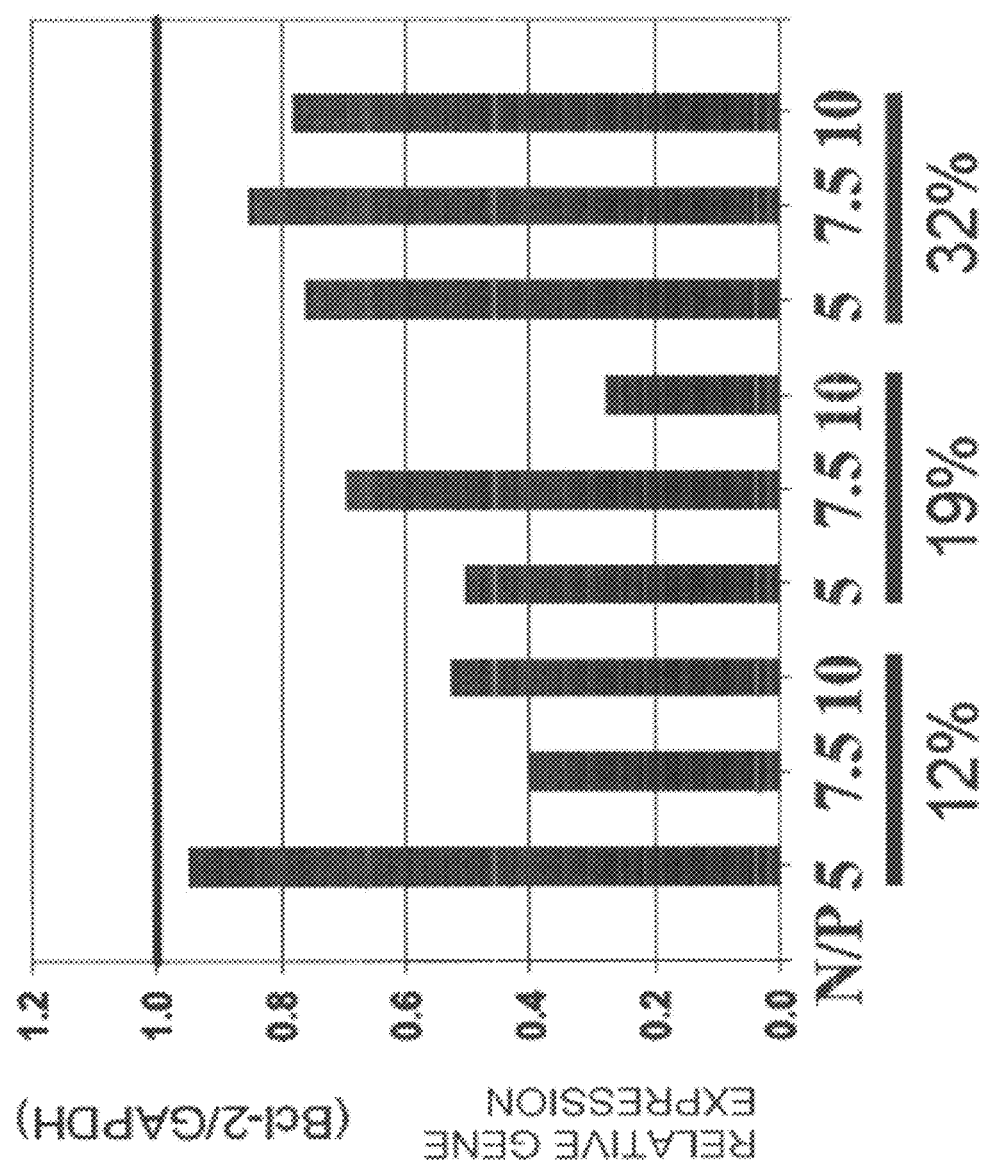
FIG. 4 is a graph illustrating the results of a knockdown test of an endogenous gene Bcl-2 using the PIC of Example 2(1).
Figure 5:
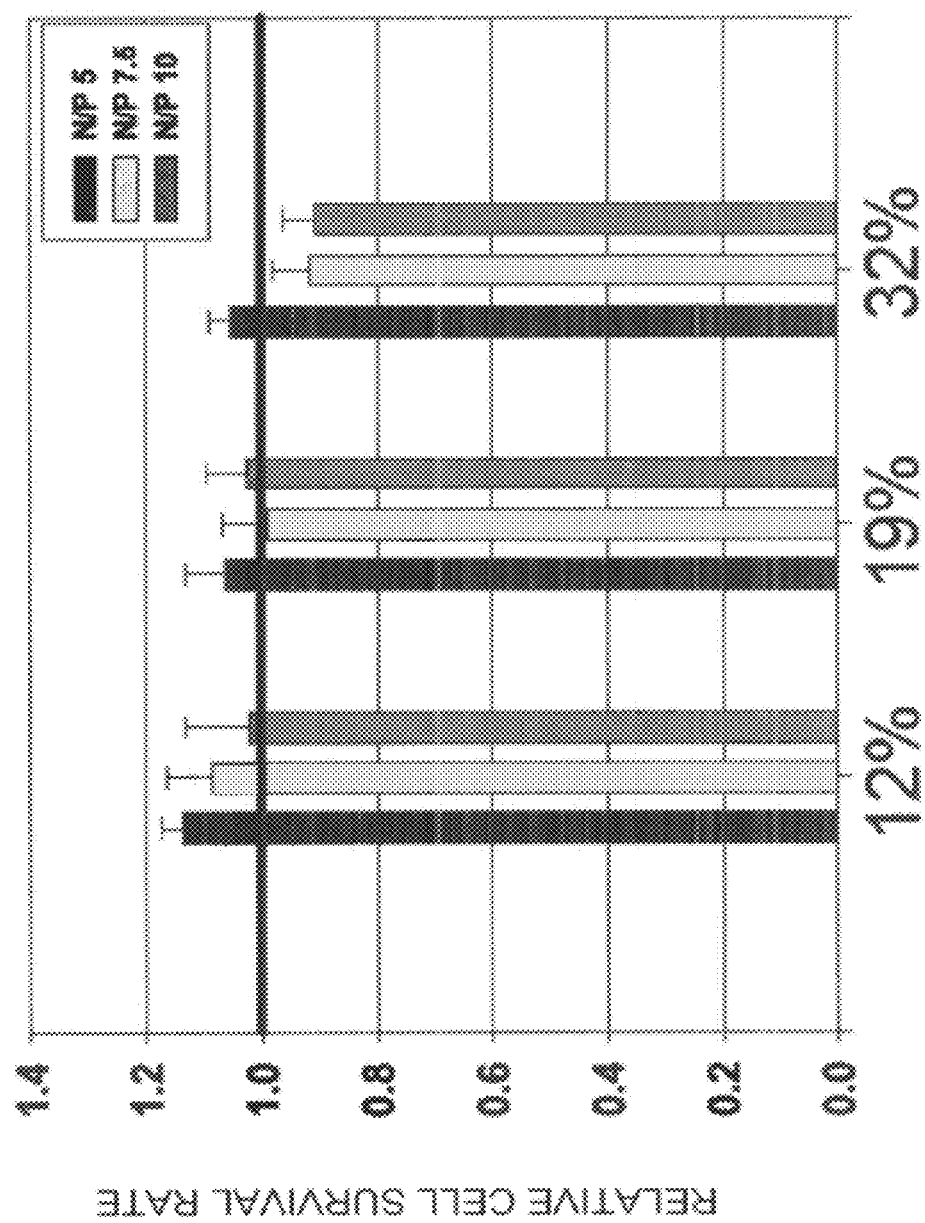
FIG. 5 is a graph illustrating the evaluation results of cytotoxicity in the knockdown test using the PIC in Example 2(1).

Human pancreatic cancer Panc-1 cells were seeded in a 6-well plate (100,000 cells/well) and were cultured overnight. Then, a complex of siRNA directed against Bcl-2 and each of PAsp(DET) and PAsp(DET)-ST was formed as described above and cultured with the cells for 48 hours (siRNA concentration: 100 nM). After that, the cells were collected by trypsinization and total RNA was collected with an Rneasy Mini kit (Qiagen). Next, cDNA was prepared using a TAKARA PrimeScript RT reagent kit and the mRNA amounts of Bcl-2 and GADPH (housekeeping gene as an internal standard) were evaluated by Real time PCR (ABI7500 Fast Real-Time PCR System (Applied Biosystems, Foster City, Calif., USA)) using a QuantiTect SYBR Green PCR kit (Qiagen). Here, the following sequence was used as the siRNA directed against Bcl-2 (5'-CAG GAC CUC GCC GCU GCA GAC-3' (SEQ ID NO: 1); 3'-CGG UCC UGG AGC GGC GAC GUC UG-5' (SEQ ID NO: 2)) (Reference 1). The results revealed that PAsp(DET)-ST 12% and PAsp(DET)-ST 19% were able to knock down mRNA of Bcl-2, which was an endogenous gene and was apoptosis-suppressive, at an N/P ratio of 7.5 or more and at any N/P ratio, respectively (FIG. 4). Further, non-specific cytotoxicity on the Panc-1 cells due to the siRNA transfection (culture for 40 hours) was evaluated using a Cell Counting Kit-8 (Dojindo, Japan). As a result, no cytotoxicity was observed at any stearoyl group introduction rate and N/P ratio (FIG. 5).

(2) Knockdown of Endogenous Gene VEGF with PAsp(DET)-ST/siRNA Complex

Figure 6:
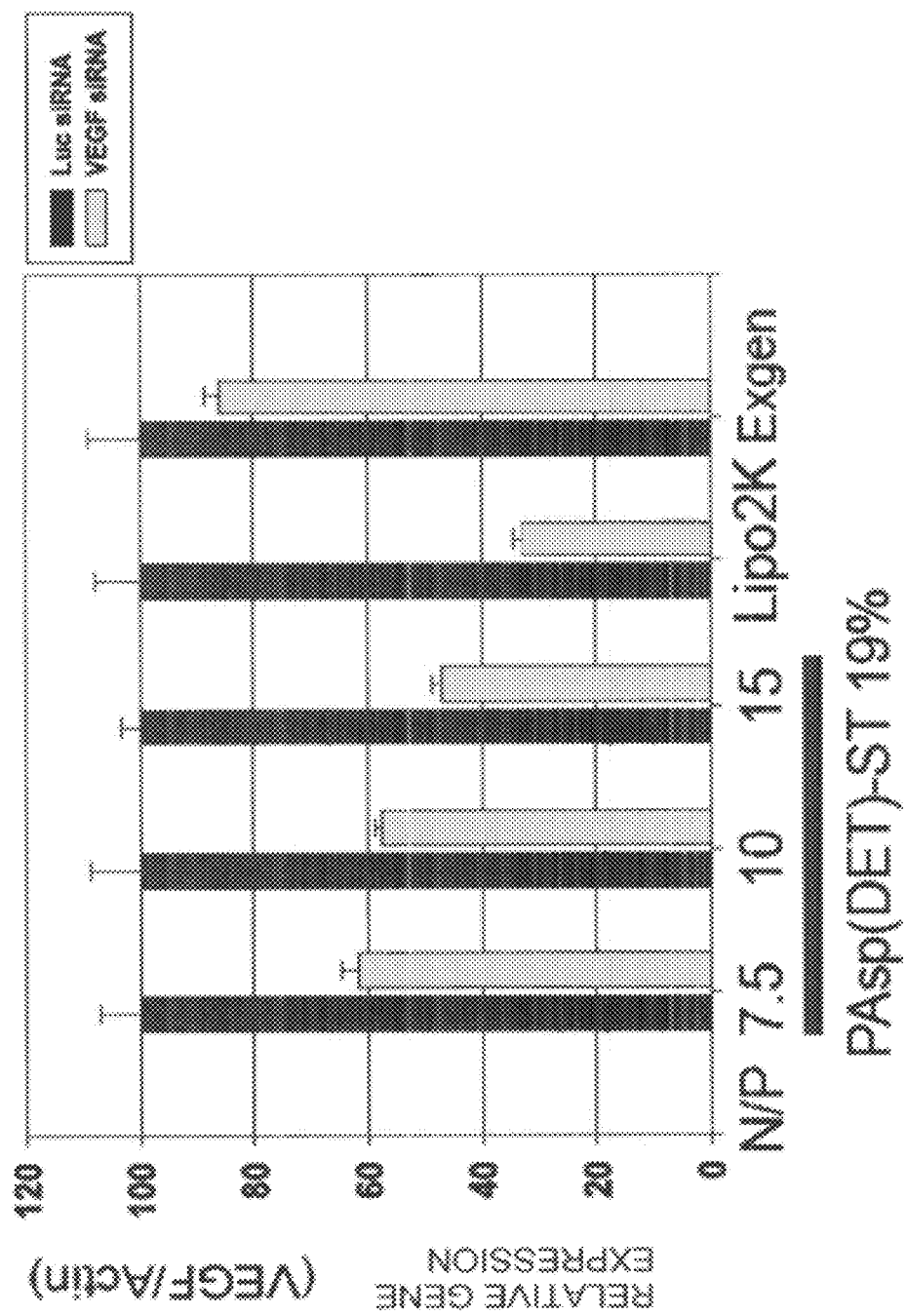
FIG. 6 is a graph illustrating the results of a knockdown test of an endogenous gene VEGF using the PIC in Example 2(2) (evaluation of VEGF expression).
Figure 7:
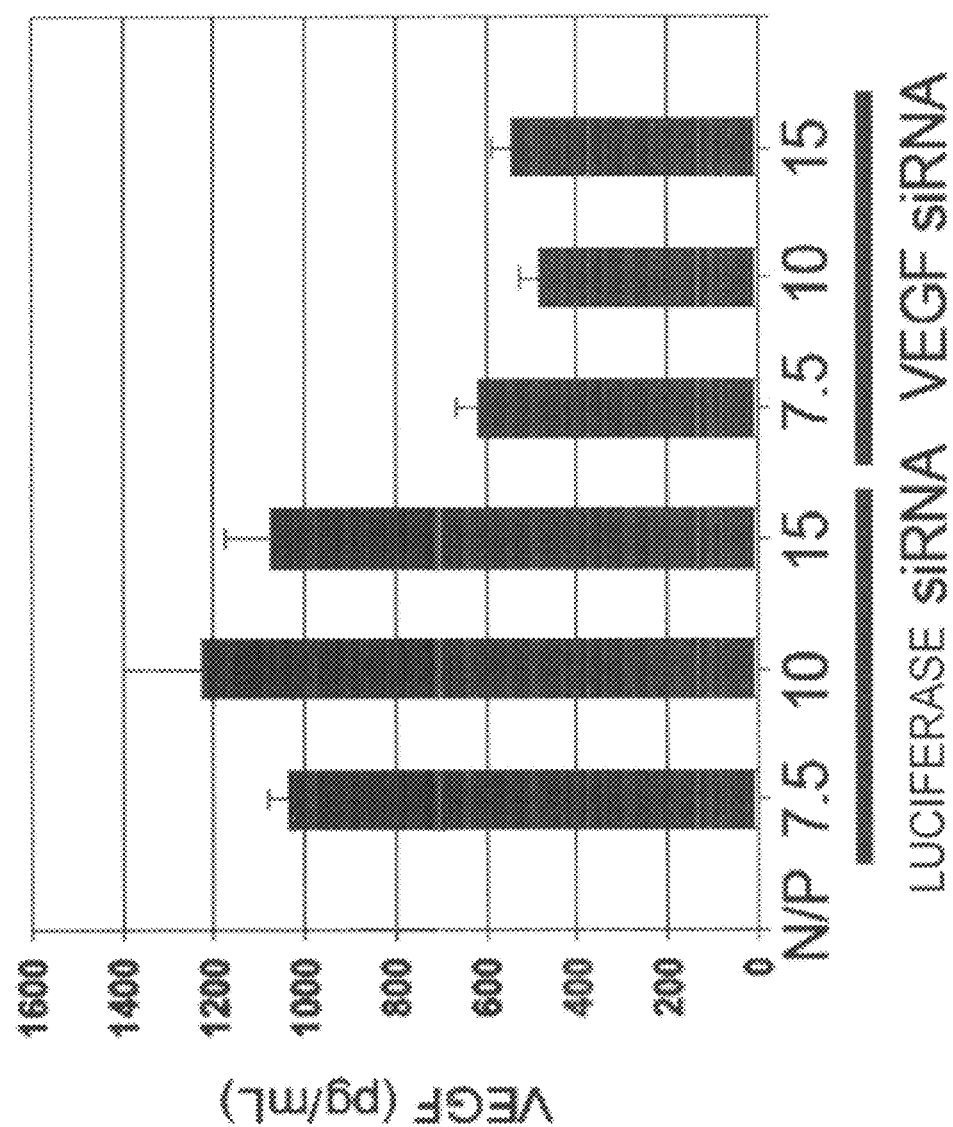
FIG. 7 is a graph illustrating the results of the knockdown test of the endogenous gene VEGF using the PIC in Example 2(2) (evaluation of VEGF at a protein level).

Complexes prepared by mixing PAsp(DET)-ST 19% and siRNA at different N/P ratios were cultured with human cervical cancer HeLa cells for 48 hours, and the mRNA amount of vascular endothelial growth factor (VEGF) was quantitatively determined by Real time PCR (using actin as an internal standard) in the same manner as described above (FIG. 6). Here, the sequence of siRNA directed against VEGF used was as described below (GGA GUA CCC UGA UGA GAU CdTdT (SEQ ID NO: 3); GAU CUC AUC AGG GUA CUC CdTdT (SEQ ID NO: 4)). As a result, PAsp(DET)-ST 19% significantly knocked down the expression of VEGF at any N/P ratio, and the activity was similar to that of Lipofectamine 2000 used as a positive control (FIG. 6). On the other hand, PEI (ExGen) did not give any significant gene knockdown effect (FIG. 6). Next, the expression amount of VEGF at a protein level was evaluated by an ELISA (sandwich immunoassay kit (DVE00, Quantkine® human VEGF, R&D Systems, Minneapolis, Minn.)). The results revealed that PAsp(DET)-ST 19% suppressed the expression amount of VEGF in a sequence-specific manner at a protein level as well (FIG. 7).

Example 3

(1) Synthesis of PEG-SS-PAsp(DET)-ST

PEG-SS-PAsp(DET) in which polyethylene glycol (PEG) and PAsp(DET) were linked through a disulfide (SS) bond undergoing cleavage in a living body was synthesized in accordance with Reference 2. Specifically, BLA-NCA was subjected to ring-opening polymerization using PEG-SS-$NH_2$ as an initiator in methylene chloride to afford PEG-SS-PBLA having a PBLA polymerization degree of 59 and 98. Next, PEG-SS-PBLA was dissolved in NMP and subjected to a reaction with DET at 5° C. for 40 minutes. After that, the reaction product was neutralized with a 25% acetic acid aqueous solution, dialyzed against 0.01 N HCl at 4° C., and further lyophilized to synthesize 0.27 g of PEG-SS-PAsp(DET).

Figure 8:
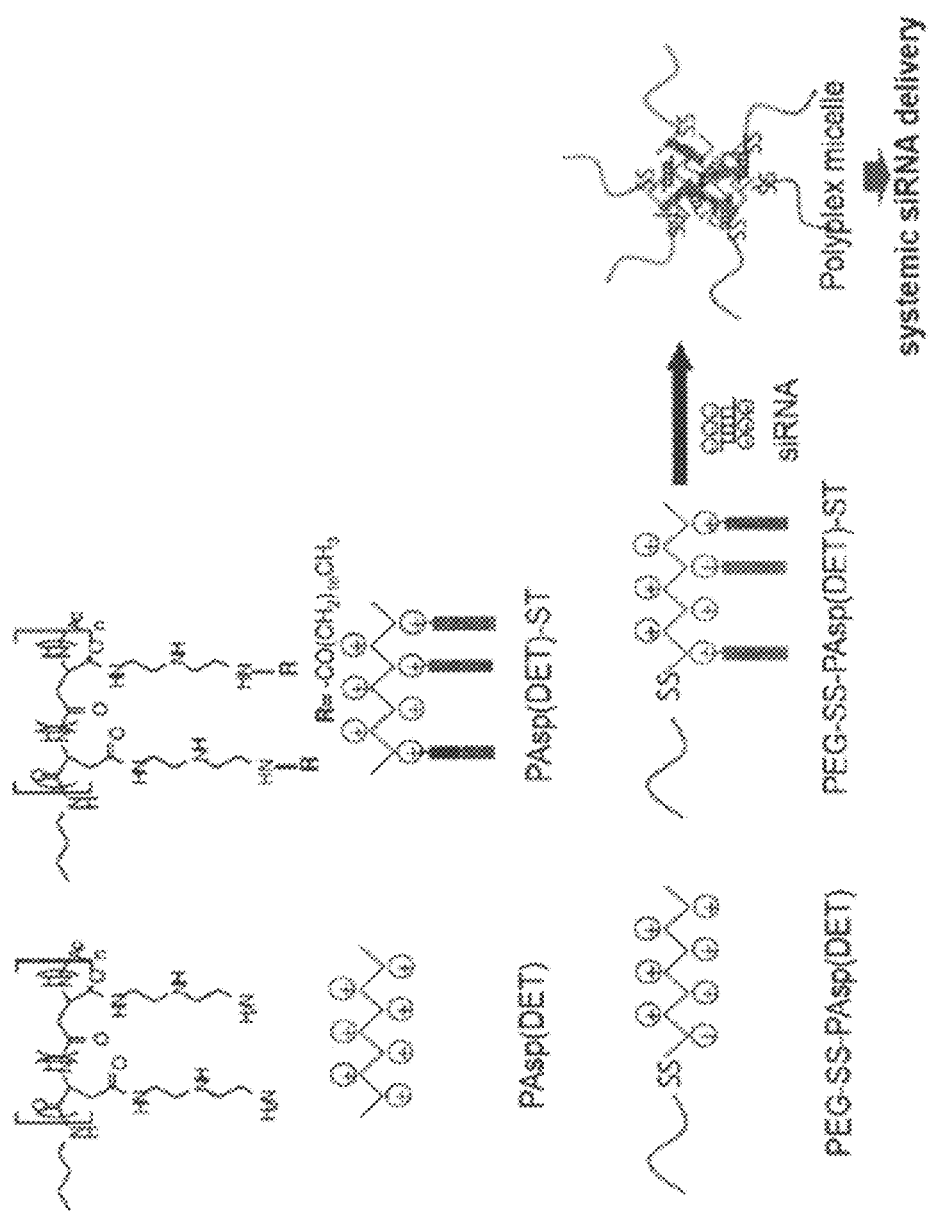
FIG. 8 is a conceptual diagram illustrating polymer micelle formation of PEG-SS-PAsp(DET)-ST and siRNA synthesized in Example 3 (1).

Next, an introduction reaction of a stearoyl group into a PAsp(DET) side chain of PEG-SS-PAsp(DET) was carried out. The introduction reaction of a stearoyl group was carried out by a reaction with N-succinimidyl octadecanoate in the same manner as in Example 1. Here, PEG-SS-PAsp(DET) polymers having PAsp(DET) polymerization degrees of 59 and 98, respectively, were subjected to a reaction with N-succinimidyl octadecanoate in an amount corresponding to 20% of a side chain primary amino group. As a result, PEG-SS-PAsp(DET)-ST polymers having stearoyl groups introduced into 17% and 19% of the side chain, respectively, were synthesized. Those polymers were dissolved in a 10 mM HEPES buffer (pH 7.3) and mixed with siRNA so as to achieve N/P=5.0 to form complexes. The thus formed complexes are each conceivable to have a polymer micelle structure in which a PAsp(DET)-ST/siRNA complex is covered with a biocompatible PEG outer envelope. In addition, PEG is gradually detached in a living body and thus both of high stability in blood and efficient siRNA introduction in a target tissue are conceivable to be simultaneously achieved in siRNA delivery through systemic administration (FIG. 8).

(2) Evaluation of Intracellular Uptake of PEG-SS-PAsp(DET)-ST/siRNA Complex

A PEG-SS-PAsp(DET)-ST/siRNA complex (N/P=5.0) is estimated to have a bilayer structure in which a surface is covered with a PEG outer envelope, and hence has a possibility of undergoing an intracellular uptake different from a PAsp(DET)-ST/siRNA complex having a cationic surface. In view of the foregoing, a complex was formed using siRNA labeled with a fluorescent dye Cy5 and evaluated for its intracellular uptake amount. HeLa cells (100,000 cells/well) were cultured on a 6-well multiplate and cultured with PAsp (DET)-ST/siRNA complex and PEG-SS-PAsp(DET)-ST/siRNA complex for 3 hours. After that, trypsinization was carried out and the average fluorescence intensity of Cy5 taken up into the cells was evaluated by flow cytometry (BD™ LSR II flow cytometer). Table 1 shows the results.

TABLE 1

| siRNA concentration | PAsp (DET)-ST | PEG(10k)-SS-PAsp(DET)(59)-ST | PEG(10k)-SS-PAsp(DET)(98)-ST |
|---|---|---|---|
| 100 nM | 9215.47 | 1688.86 | 1265.89 |
| 300 nM |  | 6079.30 | 4542.10 |
| 500 nM |  | 13935.21 | 7071.59 |

The results revealed that, when the siRNA concentration was 100 nM, the intracellular uptake amount of the PEG-SS-PAsp(DET)-ST/siRNA complex was lower than that of PAsp(DET)-ST/siRNA, but the PEG-SS-PAsp(DET)-ST/siRNA complex was taken up into the cells in an amount similar to that of PAsp(DET)-ST/siRNA by increasing the concentration of the complex.

(3) siRNA Transfection with PEG-SS-PAsp(DET)-ST/siRNA Complex

Figure 9:
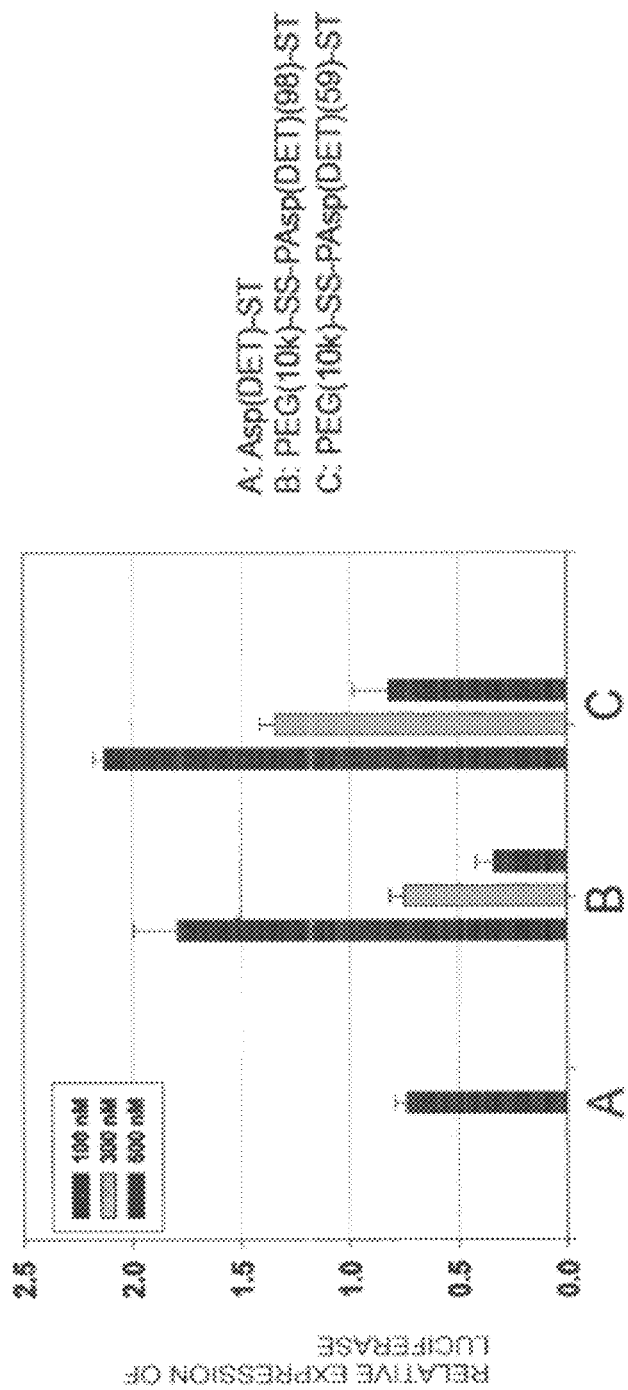
FIG. 9 is a graph illustrating the results of an siRNA transfection test using a complex of PEG-SS-PAsp(DET)-ST and siRNA of Example 3(3).

Human hepatic cancer Huh-7 cells were seeded into a 24-microwell plate (20,000 cells/well) and cultured overnight. After that, plasmid DNA that can express Firefly luciferase and Renilla luciferase was introduced into the cell using Lipofectamine 2000 (Invitrogen). After 4 hours, each of siRNA complexes formed from PAsp(DET)-ST 19%, PEG-SS-PAsp(DET) (59)-ST 17%, and PEG-SS-PAsp(DET) (98)-ST 19% each carrying siRNA directed against Firefly luciferase was added to a medium and cultured for 48 hours. After that, gene knockdown efficiency with siRNA was calculated based on the expression amount of Firefly luciferase to Renilla luciferase using a Dual-Luciferase Reporter Assay Kit (Promega). As a result, in 100 nM siRNA, the PEG-SS-PAsp(DET)-ST/siRNA complex did not exhibit any significant gene knockdown effect, whereas in 300 and 500 nM siRNA, the complex exhibited a concentration-dependent gene knockdown activity (FIG. 9). The results are in good consistent with the results of an intracellular uptake in Table 1. Thus, a complex having a polymer micelle structure is conceivable to be taken up into cells and then efficiently escaped from the endosome, which allows a function of siRNA to be efficiently expressed in the cytoplasm.

Reference 1

M. Ocker, D. Neureiter, M. Lueders, S. Zopf, M. Ganslmayer, E. G. Hahn, C. Herold, D. Schuppan, Gut 54: 1298-1308 (2005)

Reference 2

S. Takae, Y. Akiyama, Y. Yamasaki, Y. Nagasaki, K. Kataoka, Colloidal Au replacement assay for highly sensitive quantification of low molecular weight analytes by surface plasmon resonance. Bioconjugate Chem. 18(4): 1241-1245 (2007)

The invention claimed is:

1. A cationic poly(amino acid) of formula (1):

$$R^1\text{—}(COCHNH)_{n-y}\text{—}(COR^{3b}CHNH)_{y}\text{—}R^2,\quad (1)$$

with side chains $R^{3a}$—C(=O)—$R^{4a}$ on the first repeat unit and C(=O)—$R^{4b}$ on the second repeat unit wherein:

$R^1$ is a hydroxyl group, an unsubstituted or substituted linear or branched alkyloxy group having 1 to 12 carbon atoms, an unsubstituted or substituted linear or branched alkenyloxy group having 2 to 12 carbon atoms, an unsubstituted or substituted linear or branched alkynyloxy group having 1 to 12 carbon atoms, or an unsubstituted or substituted linear or branched alkyl-substituted imino group having 1 to 12 carbon atoms;

$R^2$ is a hydrogen atom, an unsubstituted or substituted linear or branched alkyl group having 1 to 12 carbon atoms, or an unsubstituted or substituted linear or branched alkylcarbonyl group having 1 to 24 carbon atoms;

$R^{3a}$ and $R^{3b}$ are each independently a methylene group or an ethylene group;

$R^{4a}$ and $R^{4b}$ are each independently selected from the group consisting of:

$$\text{—NH—}(CH_2)_{p1}\text{—}[NH\text{—}(CH_2)_{q1}\text{—}]_{r1}NH_2 \quad (i);$$

$$\text{—NH—}(CH_2)_{p2}\text{—}N[\text{—}(CH_2)_{q2}\text{—}NH_2]_2 \quad (ii);$$

$$\text{—NH—}(CH_2)_{p3}\text{—}N\{[\text{—}(CH_2)_{q3}\text{—}NH_2]\\ [\text{—}(CH_2)_{q4}\text{—}NH]_{r2}H\} \quad (iii); \text{ and}$$

$$\text{—NH—}(CH_2)_{p4}\text{—}N\{\text{—}(CH_2)_{q5}\text{—}N[\text{—}(CH_2)_{q6}\text{—}\\ NH_2]_2\}_2 \quad (iv),$$

wherein:
p1 to p4, q1 to q6, and r1 and r2 are each independently an integer of 1 to 5;
in 5 to 40% of all of the $R^{4a}$ and $R^{4b}$ groups, one hydrogen atom of at least one amino group is substituted with (i) an acyl group having a saturated or unsaturated linear or branched aliphatic hydrocarbon residue having 6 to 27 carbon atoms, or (ii) a steroloxycarbonyl group;
n is an integer of 30 to 5,000; and
y is an integer of 0 to 5,000,
provided that, when $R^{3a}$ and $R^{3b}$ are each a methylene group, y is less than n,
when n is less than y, n−y is set equal to zero, and
when n does not equal y and when y does not equal zero, the units having a number of repetitions n−y and the units having a number of repetitions y may be arranged in any order.

2. The poly(amino acid) of claim 1, wherein $R^{3a}$ and $R^{3b}$ are each a methylene group in formula (1).

3. The poly(amino acid) of claim 2, wherein:
$R^{4a}$ and $R^{4b}$ are each independently the group:

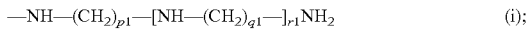

—NH—(CH$_2$)$_{p1}$—[NH—(CH$_2$)$_{q1}$—]$_{r1}$NH$_2$      (i);

wherein:
p1 and q1 are each independently 2 or 3; and r1 is an integer of 1 to 3; and
in 10 to 30% of all of the $R^{4a}$ and $R^{4b}$ groups, one hydrogen atom of at least one amino group is substituted with an acyl group having a saturated or unsaturated linear or branched aliphatic hydrocarbon residue having 6 to 27 carbon atoms.

4. The poly(amino acid) of claim 3, wherein n is 60 to 150.

5. A polyion complex, comprising:
the poly(amino acid) of claim 4, wherein the acyl group is a stearoyl group; and
siRNA having a length of 18-30 bases bound to the poly(amino acid).

6. The poly(amino acid) of claim 1, wherein $R^{3a}$ is an ethylene group and y is 0 in formula (1).

7. The poly(amino acid) of claim 6, wherein:
$R^{4a}$ is the group:

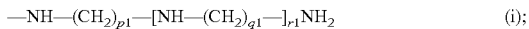

—NH—(CH$_2$)$_{p1}$—[NH—(CH$_2$)$_{q1}$—]$_{r1}$NH$_2$      (i);

wherein:
p1 and q1 are each independently 2 or 3; and r1 is an integer of 1 to 3; and
in 10 to 30% of all of the $R^{4a}$ groups, one hydrogen atom of at least one amino group is substituted with an acyl group having a saturated or unsaturated linear or branched aliphatic hydrocarbon residue having 6 to 27 carbon atoms.

8. The poly(amino acid) of claim 1, wherein:
$R^{4a}$ and $R^{4b}$ are each independently a the group:

—NH—(CH$_2$)$_{p1}$—[NH—(CH$_2$)$_{q1}$]$_{r1}$NH$_2$      (i)

wherein:
p1 and q1 are each independently 2 or 3; and r1 is an integer of 1 to 3; and
in 10 to 30% of all of the $R^{4a}$ and $R^{4b}$ groups, one hydrogen atom of at least one amino group is substituted with an acyl group having a saturated or unsaturated linear or branched aliphatic hydrocarbon residue having 6 to 27 carbon atoms.

9. A polyion complex, comprising:
the poly(amino acid) of claim 1; and
a nucleic acid.

10. The complex of claim 9, wherein the nucleic acid is selected from the group consisting of plasmid DNA, siRNA, micro RNA, an antisense nucleic acid, a decoy nucleic acid, an aptamer, and a ribozyme.

11. The poly(amino acid) of claim 1, wherein $R^{4a}$ and $R^{4b}$ are the same group.

12. The poly(amino acid) of claim 1, wherein p1 to p4 and q1 to q6 are each independently 2 or 3.

13. The poly(amino acid) of claim 1, wherein p1 to p4 and q1 to q6 are each 2.

14. The poly(amino acid) of claim 1, wherein r1 and r2 are each independently an integer of 1 to 3.

15. The poly(amino acid) of claim 1, wherein $R^1$ is a hydroxyl group.

16. The poly(amino acid) of claim 1, wherein $R^1$ is an unsubstituted or substituted linear or branched alkyloxy group having 1 to 12 carbon atoms.

17. The poly(amino acid) of claim 1, wherein $R^1$ is an unsubstituted or substituted linear or branched alkenyloxy group having 2 to 12 carbon atoms.

18. The poly(amino acid) of claim 1, wherein $R^1$ is an unsubstituted or substituted linear or branched alkynyloxy group having 1 to 12 carbon atoms.

19. The poly(amino acid) of claim 1, wherein $R^1$ is an unsubstituted or substituted linear or branched alkyl-substituted imino group having 1 to 12 carbon atoms.

20. A block copolymer of formula (2):

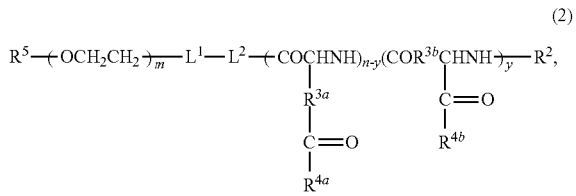

(2)

wherein:
$R^2$ is a hydrogen atom, an unsubstituted or substituted linear or branched alkyl group having 1 to 12 carbon atoms, or an unsubstituted or substituted linear or branched alkylcarbonyl group having 1 to 24 carbon atoms;
$R^{3a}$ and $R^{3b}$ are each independently a methylene group or an ethylene group;
$R^{4a}$ and $R^{4b}$ are each independently selected from the group consisting of:

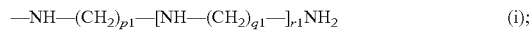

—NH—(CH$_2$)$_{p1}$—[NH—(CH$_2$)$_{q1}$—]$_{r1}$NH$_2$      (i);

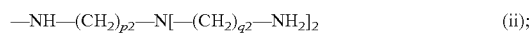

—NH—(CH$_2$)$_{p2}$—N[—(CH$_2$)$_{q2}$—NH$_2$]$_2$      (ii);

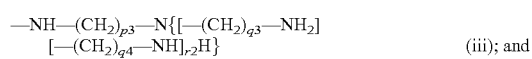

—NH—(CH$_2$)$_{p3}$—N{[—(CH$_2$)$_{q3}$—NH$_2$]
[—(CH$_2$)$_{q4}$—NH]$_{r2}$H}      (iii); and

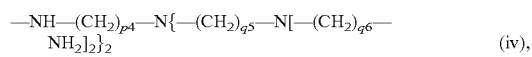

—NH—(CH$_2$)$_{p4}$—N{—(CH$_2$)$_{q5}$—N[—(CH$_2$)$_{q6}$—NH$_2$]$_2$}$_2$      (iv), wherein:
p1 to p4, q1 to q6, and r1 and r2 are each independently an integer of 1 to 5;
in 5 to 40% of all of the $R^{4a}$ and $R^{4b}$ groups, one hydrogen atom of at least one amino group is substituted with (i) an acyl group having a saturated or unsaturated linear or branched aliphatic hydrocarbon residue having 6 to 27 carbon atoms, or (ii) a steroloxycarbonyl group;
n is an integer of 30 to 5,000; and
y is an integer of 0 to 5,000, provided that, when $R^{3a}$ and $R^{3b}$ each represent a methylene group, y is less than n, when n is less than y, n−y is set equal to zero, and when n does not equal y and when y does not equal zero, the units having a number of repetitions n−y and the units having a number of repetitions y may be arranged in any order;

$L^1$ is —S—S— or a valence bond;

$L^2$ is —NH—, —O—, —O(CH$_2$)$_{p1}$—NH—, or -$L^{2a}$-(CH$_2$)$_{q1}$-$L^{2b}$-, wherein: p1 and q1 are each independently an integer of 1 to 5; $L^{2a}$ is OCO, OCONH, NHCO, NHCOO, NHCONH, CONH, or COO; and $L^{2b}$ is NH or O;

$R^5$ is a hydrogen atom or an unsubstituted or substituted linear or branched alkyl group having 1 to 12 carbon atoms; and m is an integer of 30 to 20,000.

21. A polyion complex, comprising:
the block copolymer of claim 20; and
a nucleic acid.

22. The complex of claim 21, wherein the nucleic acid is selected from the group consisting of plasmid DNA, siRNA, micro RNA, an antisense nucleic acid, a decoy nucleic acid, an aptamer, and a ribozyme.

23. The block copolymer of claim 20, wherein:
$R^{3a}$ and $R^{3b}$ are each independently represent a methylene group,
$R^{4a}$ and $R^{4b}$ are each independently the group:

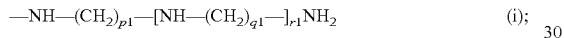

wherein:
p1 and q1 are each independently 2 or 3;
r1 is an integer of 1 to 3;
n is 60 to 150 and
in 10 to 30% of all of the $R^{4a}$ and $R^{4b}$ groups, one hydrogen atom of at least one amino group is substituted with an acyl group having a saturated or unsaturated linear or branched aliphatic hydrocarbon residue having 6 to 27 carbon atoms.

24. A polyion complex, comprising:
the block copolymer of claim 23, wherein the acyl group is a stearoyl group; and
siRNA having a length of 18-30 bases bound to the poly(amino acid).

25. A composition of matter selected from the group consisting of the following formula (1) and formula (2):

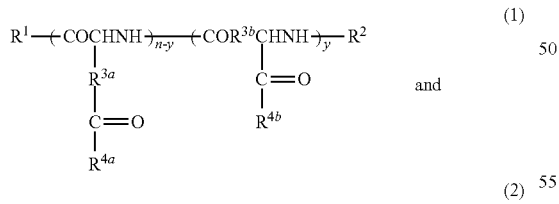

and

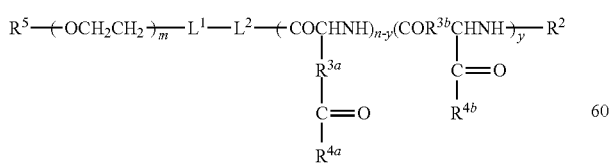

wherein:

$R^1$ is a hydroxyl group, an unsubstituted or substituted linear or branched alkyloxy group having 1 to 12 carbon atoms, an unsubstituted or substituted linear or branched alkenyloxy group having 2 to 12 carbon atoms, an unsubstituted or substituted linear or branched alkynyloxy group having 1 to 12 carbon atoms, or an unsubstituted or substituted linear or branched alkyl-substituted imino group having 1 to 12 carbon atoms;

$R^2$ is a hydrogen atom, an unsubstituted or substituted linear or branched alkyl group having 1 to 12 carbon atoms, or an unsubstituted or substituted linear or branched alkylcarbonyl group having 1 to 24 carbon atoms;

$R^{3a}$ and $R^{3b}$ are each independently a methylene group or an ethylene group;

$R^{4a}$ and $R^{4b}$ are each independently selected from the group consisting of:

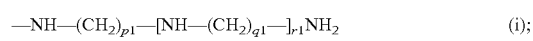 (i);

 (ii);

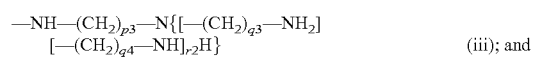 (iii); and

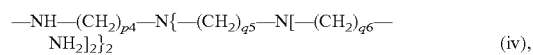 (iv), wherein:

p1 to p4, q1 to q6, and r1 and r2 are each independently an integer of 1 to 5;

in 5 to 40% of all of the $R^{4a}$ and $R^{4b}$ groups, one hydrogen atom of at least one amino group in which a hydrogen atom is substituted with (i) an acyl group having a saturated or unsaturated linear or branched aliphatic hydrocarbon residue having 6 to 27 carbon atoms, or (ii) a steroloxycarbonyl group;

n is an integer of 30 to 5,000; and y is an integer of 0 to 5,000, provided that, when $R^{3a}$ and $R^{3b}$ are each a methylene group, y is less than n, when n is less than y, n−y is set equal to zero, and when n does not equal y and when y does not equal zero, the units having a number of repetitions n−y and the units having a number of repetitions y may be arranged in any order;

$L^1$ is —S—S— or a valence bond;

$L^2$ is —NH—, —O—, —O(CH$_2$)$_{p1}$—NH—, or -$L^{2a}$-(CH$_2$)$_{q1}$-$L^{2b}$-, wherein: p1 and q1 are each independently represent an integer of 1 to 5; $L^{2a}$ is OCO, OCONH, NHCO, NHCOO, NHCONH, CONH, or COO; and $L^{2b}$ is NH or O;

$R^5$ is a hydrogen atom or an unsubstituted or substituted linear or branched alkyl group having 1 to 12 carbon atoms; and m is an integer of 30 to 20,000.

* * * * *

UNITED STATES PATENT AND TRADEMARK OFFICE
CERTIFICATE OF CORRECTION

PATENT NO. : 8,546,487 B2
APPLICATION NO. : 13/147319
DATED : October 1, 2013
INVENTOR(S) : Kazunori Kataoka et al.

Page 1 of 1

It is certified that error appears in the above-identified patent and that said Letters Patent is hereby corrected as shown below:

In the Claims

Column 17, line 26, cancel the word "represent".

Column 18, line 37-38, cancel the text "in which a hydrogen atom".

Column 18, line 56, cancel the word "represent".

Signed and Sealed this
Twentieth Day of May, 2014

Michelle K. Lee
*Deputy Director of the United States Patent and Trademark Office*